United States Patent [19]

Lawton-Wall

[11] Patent Number: 5,021,424
[45] Date of Patent: Jun. 4, 1991

[54] VITAMIN COMPOSITION FOR TREATMENT OF FLEA INFESTATION IN ANIMALS

[76] Inventor: Jennylyn Lawton-Wall, 318 D Texas Rd., Morganville, N.J. 07751

[21] Appl. No.: 359,957

[22] Filed: Jun. 1, 1989

[51] Int. Cl.[5] .................. A61K 31/51; A61K 31/415; A61K 31/34
[52] U.S. Cl. .................................. 514/276; 514/392; 514/474; 514/875
[58] Field of Search ............... 514/875, 876, 474, 276, 514/392

[56] References Cited

U.S. PATENT DOCUMENTS 4,619,829 10/1986 Motschan ........................... 514/251
4,751,085 6/1988 Gaull .................................... 514/458
4,876,090 10/1989 Weisler ............................... 514/875

Primary Examiner—Stanley J. Friedman
Assistant Examiner—Raymond J. Henley, III
Attorney, Agent, or Firm—Mathews, Woodbridge & Collins

[57] ABSTRACT

An internally administered pharmaceutical preparation for treatment and prevention of flea infestations in animals, especially dogs and cats, and the associated allergic reaction, hair loss and irritation which accompany flea infestation. The active ingredients include Vitamin C, Vitamin B-1 and Biotin in a pharmaceutically acceptable carrier. The pharmaceutical preparation is preferably administered orally, once a day to the animal.

5 Claims, No Drawings

VITAMIN COMPOSITION FOR TREATMENT OF FLEA INFESTATION IN ANIMALS

BACKGROUND OF THE INVENTION

1. Field of the Invention

This invention relates to an orally administered pharmaceutical preparation containing a combination of vitamins that eliminates flea infestation on animals, especially dogs and cats, prevents and cures the allergic reaction to flea bites, and promotes the healing of the skin and irritation associated with flea infestation.

2. Description of the Related Art

Mankind has been waging a war against fleas since prehistoric times. In fact, fleas have been found embalmed along with King Tut's cat. Early remedies included fumigation, and sulfur was used as early as 1,000 B.C. as a fumigant. Marco Polo used a sulfur based oil as a mange treatment in 1300 A.D. These early treatments and many of the treatments used today have used externally applied chemicals which provided only limited benefits for the animals and their owners.

Presently, the primary means of controlling fleas is by killing the fleas externally to the animal by the use of pesticide. Although pesticides are effective in killing fleas, they present potential health hazard to the animals and their owners who come in contact with these pesticides. The four major categories of externally applied pesticides are:

1. Inorganics—these include arsenic and mercury based compounds along with some less toxic compounds.
2. Organic compounds derived from plants—these include rotenone and the pyrethrins, these quickly kill the fleas, but usually must be applied on a regular basis.
3. Chlorinated hydrocarbons—Such as DDT, many of these compounds were once considered safe, but are now banned.
4. Acetylcholinesterase inhibitors—this group evolved as a result of nerve gas experimentation during World War II.

Aside from the health hazards associated with these pesticides, be they dips, collars, sprays or the like, none of them do anything to alleviate the hair loss, skin irritation or other allergic reaction associated with flea infestation.

Another type of remedy for flea infestation is by internal administration of the drug to the affected animal. Presently, there are several products on the marketplace which provide limited relief.

1. The newest of these is the citrus based products with the active ingredient, d-limonene, which the manufacturer claims to be deadly to fleas.
2. Another, is Cythioate, which is marketed under the trademark of Probam ®. Cythioate has been used for over twenty years, and it does kill fleas when administered internally to the dog. The problem lies in the fact that to kill the fleas the dog must first be bitten by the fleas and, Probam ® is poisonous. Accordingly, both the safety and the comfort of the animal is at risk with the use of this treatment.
3. Another is the chemical Fenthion which is marketed under the trademark Spoton ®. It is applied externally but is absorbed through the skin into the blood stream. The drawback with Fenthion is that small dogs may develop tremors of the head and neck as a result of treatment with Fenthion.
4. Lastly, another product uses elemental sulfur dissolved in a water base to which oil is added. This product is based on the old Mid-Western concept of placing a block of sulfur in the drinking water of the animals to help prevent and cure flea infestation. The manufacturers claim that they have perfected a way to "ionize" the sulfur so that it may be more readily metabolized by the animal. This sulfur based product has met with only limited success.

The following U.S. Patents are considered to be of general interest to the disclosure: U.S. Pat. Nos. 3,934,019; 4,053,593; 4,265,901; and 4,322,422.

All of these remedies listed above, which were used from 1000 B.C. to the present, address only some of the problems associated with the infestation. The manufacturers have all failed to realize that the problem is not singular but a combination of several factors. Where one product kills fleas after they bite, it does nothing to alleviate the allergic reaction which results from the bite. Another product kills fleas but does nothing for the damage already done by previous bites. Others cure infestation on the surface of the skin but do not prevent reinfestation and tape worm from ingested fleas, their eggs and larva. In addition, most of these products are toxic to both the animals and their owners.

Therefore, it is an object of this present invention to provide a single product which stops flea infestation, prevents allergic reaction to the flea bites, repairs the damage to the animal done by previous bites, kills ingested flea eggs and larva (tape worm) and prevents reinfestation of the animals. Another object of this invention is to provide a treatment for flea infestation which is completely safe to both the animals, their owners and the environment. It is still a further object of this present invention to provide a cure for flea infestation which is both easy for the owner to administer and easy to accept by the animal.

SUMMARY OF THE INVENTION

Briefly, the present invention is an internally administered pharmaceutical preparation for treatment and prevention of flea infestations in animals, especially dogs and cats, and the associated allergic reaction, hair loss and irritation which accompany flea infestation. The active ingredients include Vitamin C, Vitamin B-1 and Biotin in a pharmaceutically acceptable carrier. The pharmaceutical preparation is preferably administered orally, once a day to the animal. Preferably, Vitamin C is in a sustained time release carrier, and the active ingredients, when used for the treatment of flea infestation in dogs are included in the following proportions:

| | |
|---|---|
| Vitamin C: | 500 milligrams; |
| Vitamin B-1: | 100 milligrams; and |
| Biotin: | 800 micrograms. |

DETAILED DESCRIPTION OF THE PREFERRED EMBODIMENT

In the preferred embodiment, the present invention includes an internally administered pharmaceutical preparation for the treatment and prevention of flea infestation in animals, particularly dogs and cats. The pharmaceutical preparation of the present invention not only treats and prevents flea infestation but also treats and prevents the associated allergic reaction, hair loss and irritation which accompany flea infestation. The pharmaceutical preparation includes as the active ingredient Vitamin C, preferably in the form of a sustained time release carrier; Vitamin B-1 and Biotin, which are combined in a pharmaceutically acceptable carrier. It is preferred that the active ingredients are present in the following proportions:

| | |
|---|---|
| Vitamin C: | 50 to 1500 milligrams; |
| Vitamin B-1: | 50 to 100 milligrams; and, |
| Biotin: | 300 to 800 micrograms. |

It has been found that the best results for the treatment of dogs were obtained when the proportions of the active ingredients were:

| | |
|---|---|
| Vitamin C: | 500 milligrams; |
| Vitamin B-1: | 100 milligrams; and, |
| Biotin: | 800 micrograms. |

Preferably, the pharmaceutical preparation is made into pill form and administered orally to the animal once a day. The dosage of this pharmaceutical preparation varies according to the body weight of the animal. For small dogs and other animals weighing 1 to 19 lbs., it is preferred to use one quarter tablet, which includes:
125 milligrams of Vitamin C;
25 milligrams of Vitamin B-1; and
200 micrograms of Biotin.
For medium sized dogs and other animals weighing 20 to 40 lbs., one half ($\frac{1}{2}$) tablet is used, which contains approximately:
250 milligrams of Vitamin C;
50 milligrams of Vitamin B-1; and
400 micrograms of Biotin.
For large sized dogs and other animals weighing 41 to 80 lbs., one (1) tablet containing approximately:
500 milligrams of Vitamin C;
100 milligrams of Vitamin B-1; and
800 micrograms of Biotin.
For animals weighing over 80 lbs., it is preferred to add approximately one quarter ($\frac{1}{4}$) tablet for each additional 20 lbs. of body weight. Theoretically, the animal cannot overdose on this pharmaceutical preparation since excess vitamins are excreted in the animal's urine. However, it is preferred to limit the initial dosage to two (2) tablets per day for animals weighing 160 lbs. or more.

In tablet form, the pharmaceutical preparation can be mixed with the animal's food or administered orally directly to the animal.

INDIVIDUAL INGREDIENTS

Vitamin C, also referred to as Ascorbic Acid, has the chemical formula $C_6H_8O_6$. Vitamin C is not manufactured or stored by the body of many animals and must be replaced as needed. Vitamin C is depleted under stress due to the adrenal glands. An animal can need up to five times more Vitamin C than normal during stress period. Accordingly, it is necessary to use a sustained release containing carrier in the pharmaceutical preparation. Vitamin C exerts a stimulant action on the defensive mechanisms embodied and also reduces the effects of many allergic reactions by activating histamines.

Metabolization of Vitamin C in its synthesis is mediated by a dependent and enhanced by the actions of Biotin. In addition, Vitamin C increases the acidity of the animal's digestive tract and this increased acidity helps to kill ingested fleas, their eggs and tape worm (flea larva). Lastly, Vitamin C helps maintain and stabilize Vitamin B-1 in the animal's system since Vitamin B-1 is destroyed in normal or alkaline solution.

Vitamin B-1, also referred to as Thiamine, is used mostly in the form of chlorihehydrochloride (usually designated as Thiamine hydrochloride). The empirical formula of Thiamine hydrochloride is $C_{12}H_{17}ON_4ClS.HCl$. Vitamin B-1 cannot be stored or synthesized in the animal's body in any great amounts and is also depleted during stress.

Vitamin B-1 in its pure state is easily taken up and metabolized by the animal's body. This is opposed to sulfur compounds which are not easily metabolized by the animal's body. Vitamin B-1 breaks down in an alkaline solution, however, the acidity of Vitamin C allows Vitamin B-1 to be stabilized in the animal's body and maintain its activity within the animal. The action of Vitamin C as it applies to the treatment of flea infestation is not well understood, however, inventor believes that Vitamin B-1 acts by regulating the citric acid cycle in releasing both sulfur (which is a breakdown product of Vitamin B-1) and citric acid based compounds, which act to kill fleas on the animal's skin. Also, Vitamin B-1 may help in controlling stress in the animal which leads to reduced depletion of all vitamins needed by the animals.

Biotin, otherwise known as Vitamin H, has the molecular formula of $C_{10}H_{16}O_3N_2S$. Biotin, like Vitamin C and Vitamin B-1 is not stored in the animal's body, is easily depleted and must be replaced daily. Biotin is needed for the metabolization and synthesis of Vitamin C. Biotin also works to alleviate eczema and dermatitis in animals especially dogs. One sign of Biotin deficiency in dogs is depigmentation and loss of hair. This same condition is also seen in dogs suffering from flea infestation. However, when Biotin is replaced and maintained in the animal's system, depigmentation and hair loss is stopped and growth and pigmentation of the hair is observed.

Although each of these vitamins, Vitamin C, Vitamin B1 and Biotin, have individual beneficial effects on the animal, it is only when combined in the proportions described above that their synergistic effect is observed in the control and cure of the flea infestation and its symptoms. One must understand that the problem of flea infestation is a combination of many factors, and not confined to the mere ridding an animal of the fleas. One flea bite on an animal which is allergic to the saliva of the flea can cause as much damage to the animal as thousands of flea bites on an animal which is not allergic.

Dog Flea, *Ctenocephali canis,* Life Cycle

1. The dog is exposed to fleas through its contacts with outside environment or even contacts with other flea infested dogs. The flea, in this case *Ctenocephali canis,* a parasitic insect which utilizes dogs as its primary host, bites the dog in order to obtain a blood meal.

2. Frequently, the dog will have an allergic reaction to the flea saliva, not unlike the response exhibited by humans when bitten by mosquitoes, black flies and even fleas.

3. This allergic reaction results in a "hot spot". In response to the irritation, the dog begins to chew the irritated area. The result of this continuous chewing by the dog is swallowing and ingesting fleas and their eggs.

4. The dog develops more irritation from the allergic reaction and from its own chewing of the area. This irritation introduced by the dog itself coupled with the allergic reaction produces hair loss and severe itching. Thus, the animal becomes entangled in a positive feedback cycle where chewing and additional flea bites continue to result in more skin irritation and greater areas of hair loss. It is not uncommon to find dogs who are especially suspectable to flea bite allergies to develop mange-like conditions over the greater part of the body during the flea season.

5. A common complication of the cycle is infection with tape worms as a consequence of ingesting fleas and the eggs which also harbor this parasite.

6. Dog feces contain flea larva thereby reinfecting the environment the environment to again infest dogs which happen to come into contact with them.

EXPERIMENTS

Experiment 1

The inventor, through her experience and supervising town owned dog kennels and a dog grooming shop, had observed that dogs which were fed high amounts of vitamins and dietary supplements showed greater resistance to flea infestation than dogs who only received a normal diet. Accordingly, on June 12, 1984, the inventor began an experiment to determine whether any one or a combination of the vitamins and dietary supplements were especially effective in preventing flea infestation and the accompanying symptoms. The inventor selected two dogs:

Dog No. 1—Chris, female, otter hound, age: 3 yrs., fur: long coat, weight: 68 lbs.

Dog No. 2—Ziggy, mixed shepherd male, age: 10 yrs., fur: short coat, weight: 31 lbs.

Both dogs were on placed on varying vitamin and dietary supplements over a five month period ending on Dec. 9, 1984.

| Vitamins and Minerals | Dog #1 weight: 68 lbs. | Dog #2 weight: 31 lbs. |
| --- | --- | --- |
| Pervinal | 2 tablets | 1 tablet |
| Therolin | 1 tablet | ½ tablet |
| Wheat Germ | 1 tablespoon | ½ tablespoon |
| Mira Coat | 1 tablespoon | 1 teaspoon |
| Vegetable Oil | 1 tablespoon | ½ tablespoon |
| Vitamin A | 10,000 IU | 5,000 IU |
| Vitamin E | 400 mg | 200 mg |
| Biotin | 100 mcg | 50 mcg |
| Kelp | 2 tablets | 1 tablet |
| Vitamin B-1 | 200 mg | 100 mg |
| Vitamin C (sustained release) | 1500 mg | 500 mg |

On Day No. 1, June 12, 1984, each dog was given its respective vitamin-mineral formulation and dipped to kill all fleas. Both dogs were walked daily on untreated property where many flea infested dogs were also walked.

The first two week test period involved feeding both animals the above formulation minus the Pervinal and the Viomate vitamins. Viomate vitamins are a proprietary vitamin formulated specifically for dogs. No change was noted in flea resistance. Pervianl and Viomate were discontinued as part of the experiment.

During the second two week test period, June 17, 1984 to July 10, 1984, the formulation was changed to exclude the above, wheat germ oil and vegetable oil. Again no change was noted in flea resistance in that the animals remained free of fleas despite living in a normal environment permitting exposure to fleas.

During the third two week test period, July 10, 1984 through July 25, 1984, the formula was changed to eliminate the above, vitamin A and vitamin E. The coat of animal #1 changed texture slightly. Since the animal's food was deficient in oils, it was concluded that this was a normal reaction to the dog lacking oil in her diet. However, no change was noted in flea resistance as both animals continued to remain flea free.

The fourth two week test period, July 26, 1988 to Aug. 8, 1984, the formula was changed to eliminate the above, Biotin and Kelp. No direct sighting of fleas was observed but evidence of irritation on animal #1's tail was evident. The rash was typical of that found with an allergic reaction to flea bites.

Even though finding no direct evidence of fleas, some dogs will still have a problem that can result from a single flea. By the end of test period, slight evidence of flea excrement on animal #1 was found, even though no direct evidence of fleas was observed. Therefore, the animal must have been bitten by one or more fleas during the test period.

The conclusion was that either Kelp or Biotin helped stop or prevent the allergic reaction experienced with flea bites. Both animals appeared to remain free of flea infestation.

During the next test period, the length of time was increased to four weeks from Aug. 9, 1984 to Sept. 8, 1984. The research focused on determining whether Biotin or Kelp or both was responsible for preventing the allergic reaction.

The formula used was the same used for the prior test period with the Kelp added back in. At the end of the test period, animal #1's back had become inflamed and easily irritated. Also, hair loss on this animal was noticeable. Flea dirt and some evidence of fleas with counts under ten was found.

Dog #2 also showed evidence of flea rash but not as severe as dog #1. The flea count on dog #2 was less than five.

It was concluded that Kelp was ineffective in preventing the allergic reaction nor repelling fleas.

The next test period from Sept. 9, 1984 to Oct. 8, 1984 was designed to confirm the efficacy of Biotin in preventing allergic reaction from flea bites. A formulation of Biotin, vitamin C and vitamin B1 was fed to the test animals. Noticeable decreases in the dog #1's skin redness was evidenced. Also, dog #2 appeared to be itching less.

By the end of test period, no fleas were found on either dog and new hair growth was evident. While some irritation and the attendant scratching remained but was decreasing, it was concluded that it was not due to a flea allergy but rather residual effects from prior allergic reactions.

It was concluded that Biotin, vitamin C and vitamin B1 are required to prevent flea infestation and to prevent flea bite allergic reactions.

The next test period from Oct. 8, 1984 to Nov. 9, 1984, Biotin and vitamin C were fed to the dogs to test the effect of eliminating vitamin B1. Conditions similar to the absence of Biotin appeared without the severe redness and hair loss. That is, the animals resume scratching and evidence slight flea infestation. At the end of the test period, the flea count on dog #1 was 37 and on dog #2 was 18.

It was concluded that Biotin and B1 are required to prevent flea rash.

The next test in this series was to eliminate vitamin C from the formulation. This test was conducted from Nov. 9, 1984 to Dec. 9, 1984. Time available for testing was limited until the first killing frost. While the skin was clear during this period and hair growing back, slight scratching still persisted. Flea count on the bitch was now 9. On dog #2, the count was 5. It was concluded that vitamin C was required to make enable Biotin and vitamin B1 to work more effectively.

The final test in this series commenced on Dec. 10, 1984 and ended on Dec. 17, 1984. Vitamin C was added back into the formulation. All remaining skin irritation cleared up quickly. No fleas, redness, or evidence of a flea allergy were evidenced at the conclusion of this test series.

EXPERIMENT 2

The test period was from May 3, 1985 to May 17, 1985. The same dogs in the first experiment were given only vitamin B1. After two weeks, flea problem was present and redness was evidenced on stomachs of both dogs. Hair loss was noticeable on the bitch and only slightly on the male near the tail set.

It was concluded that B1 is required for flea reduction; Biotin is needed for flea reduction and reduction of irritation, prevention of hair loss and prevention of allergic reaction; and vitamin C is required to make the other two elements function more efficiently.

EXPERIMENT 3

Dog #1—same as prior experiments.
Dog #2—same as prior experiments.
Dog #3—Misty, 90 lb., Golden Retriever, medium length coat.
Dog #4—Domino, Chihuahua, 6 lbs., short coat.

All animals were provided a formulation of vitamin C; vitamin B1; and Biotin as a daily supplement to the normal diet. This experiment was conducted during 1985. Dogs #1–#3 were initially provided daily doses of 250 mg of C; 100 mg of B1; and 800 mcg of Biotin. The results of the experiment are tabulated in FIG. 1.

After the second the second two week test period, it was decided to increase the doses of vitamin C to the larger dogs, that is, dogs #2 and #3, in that dog #1 was showing faster improvement. The vitamin C dose was doubled for dogs #2 and #3.

At the end of the July 14 test period, it was decided to determine if the smaller dogs could receive less of the formulation of B1; vitamin C; and Biotin. A small dog was added to the experiment to confirm the size dependency on the dosage.

Beginning July 29, 1985, dog #1 was given 250 mg of C; 50 mg of B1; and 400 mcg of Biotin. Dogs #2 and #3 were given 500 mg of C; 100 mg of B1; and 800 mcg of Biotin. Dog #4 was given 125 mg of C; 25 mg of B1; and 200 mcg of Biotin. All animals responded well and by the end of the test period on Sept. 8, 1985, all animals were entirely symptom free.

ADDITIONAL EXPERIMENTATION

The invention was given to other pet owners since that time to determine the success rate under normal conditions. Each recipient of the invention were required to adhere to strict protocol including description of the dog's condition in the same manner as presented in Table 1, below. The dosage of the invention was regulated according to the body weight of the dog with dogs weighing between 40 to 80 lbs. receiving a full daily dose; dogs weighing greater than 80 lbs. receiving 1.5 daily doses; dogs weighing between 20 to 40 lbs. receiving 0.5 daily doses; and dogs weighing less than 20 lbs receiving 0.25 of the daily dose.

Recipients of the medication were instructed to administer the drug over a 56 day period, noting the observable effects on the animal. The same relief in symptoms found in the controlled experiment were noted when used by pet owners.

While the invention has been described with reference to a preferred embodiment thereof, it will be appreciated by those of ordinary skill in the art that modifications can be made to the constituents that comprise the invention without departing from the spirit and scope thereof.

TABLE 1

| Test Period | Condition | #1 | #2 | #3 | #4 |
|---|---|---|---|---|---|
| June 1 to | REDNESS OF SKIN | M | M | B | |
| June 15 | HAIR LOSS | M | B | B | |
| | FLEAS | M | M | M | |
| | SCRATCHING | B | B | B | |
| June 16 to | REDNESS OF SKIN | S | M | M | |
| June 29 | HAIR LOSS | S | M | B | |
| | FLEAS | S | M | M | |
| | FLEA ALLERGY | I | B | M | |
| | SCRATCHING | M | B | B | |
| June 30 to | REDNESS OF SKIN | N | S | S | |
| July 13 | HAIR LOSS | S | S | I | |
| | FLEAS | N | N | N | |
| | FLEA ALLERGY | S | S | I | |
| | SCRATCHING | S | I | M | |
| July 14 to | REDNESS OF SKIN | N | N | N | |
| July 28 | HAIR LOSS | N | N | S | |
| | FLEAS | N | N | N | |
| | FLEA ALLERGY | N | N | S | |
| | SCRATCHING | N | N | S | |
| July 29 to | REDNESS OF SKIN | N | N | N | M |
| August 11 | HAIR LOSS | N | N | N | I |
| | FLEAS | N | N | N | I |
| | FLEA ALLERGY | N | N | N | N |
| | SCRATCHING | N | N | S | N |
| August 12– | REDNESS OF SKIN | N | N | N | S |
| August 25 | HAIR LOSS | N | N | N | S |
| | FLEAS | N | N | N | N |
| | FLEA ALLERGY | N | N | N | N |
| | SCRATCHING | N | N | N | N |
| August 26– | REDNESS OF SKIN | N | N | N | N |
| Sept. 8 | HAIR LOSS | N | N | N | N |
| | FLEAS | N | N | N | N |
| | FLEA ALLERGY | N | N | N | N |
| | SCRATCHING | N | N | N | N |

KEY:
N = NO SIGN;
S = SLIGHT;
I = INTERMEDIATE;
M = MODERATE;
B = BAD PROBLEM.

I claim:
1. A method for the treatment and prevention of flea infestation and the associated allergic reaction, hair loss and irritation in canine and feline animals which comprises administering to the animal an effective amount of a vitamin composition comprising the combination of:
   (a) about 50 to 1,500 milligrams of Vitamin C;
   (b) about 50 to 100 milligrams of Vitamin B-1; and,
   (c) about 300 to 800 micrograms of Biotin.

2. The method of claim 1 wherein said vitamin composition is administered orally.

3. The method of claim 2 wherein said vitamin composition is administered daily.

4. A method for the treatment and prevention of flea infestation and the associated allergic reaction, hair loss and irritation in canine and feline animals which comprises administering to the animal an effective amount of a vitamin composition comprising the combination of:

(a) about 50 to 1,500 milligrams of Vitamin C;
(b) about 50 to 100 milligrams of Vitamin B-1; and
(c) about 300 to 800 micrograms of Biotin wherein the said Vitamin C is present in a sustained release carrier and is administered daily and orally.

5. The method of claim 4 wherein said vitamin composition comprises the combination of:

(a) about 500 milligrams of Vitamin C;
(b) about 100 milligrams of Vitamin B-1; and,
(c) about 800 micrograms of Biotin.

* * * * *